(12) United States Patent
Van Helleputte

(10) Patent No.: US 9,610,044 B2
(45) Date of Patent: Apr. 4, 2017

(54) VARIABLE CAPACITOR CIRCUIT AND METHOD

(71) Applicant: IMEC, Leuven (BE)

(72) Inventor: Nick Van Helleputte, Korbeek Dijle (BE)

(73) Assignee: IMEC, Leuven (BE)

( * ) Notice: Subject to any disclaimer, the term of this patent is extended or adjusted under 35 U.S.C. 154(b) by 0 days.

(21) Appl. No.: 13/671,164

(22) Filed: Nov. 7, 2012

(65) Prior Publication Data

US 2013/0113549 A1    May 9, 2013

Related U.S. Application Data

(60) Provisional application No. 61/557,060, filed on Nov. 8, 2011.

(51) Int. Cl.
*H01L 27/108* (2006.01)
*A61B 5/00* (2006.01)
(Continued)

(52) U.S. Cl.
CPC .......... *A61B 5/7214* (2013.01); *A61B 5/0402* (2013.01); *A61B 5/04017* (2013.01);
(Continued)

(58) Field of Classification Search
CPC ...... H01L 29/93; H01L 29/94; H01L 27/0808
(Continued)

(56) References Cited

U.S. PATENT DOCUMENTS 4,659,997 A * 4/1987 Ferland ............... H03F 3/45076
324/123 C
5,140,966 A * 8/1992 Wong ..................... F02M 17/20
123/543

(Continued)

FOREIGN PATENT DOCUMENTS

| CN | 101422362 A | 5/2009 |
| EP | 2298164 A2 | 3/2011 |
| WO | 2009/017413 A1 | 2/2009 |

OTHER PUBLICATIONS

Hong, Sunjoo et al., "A Combined Method to Reduce Motion Artifact and Power Line Interference for Wearable Healthcare Systems", Circuits and Systems (APPCCAS), 2010 IEEE Asia Pacific Conference, Dec. 6-9, 2010, pp. 508-511.

(Continued)

*Primary Examiner* — Eva Y Montalvo
*Assistant Examiner* — Mohammad M Hoque
(74) *Attorney, Agent, or Firm* — McDonnell Boehnen Hulbert & Berghoff LLP

(57) ABSTRACT

A variable capacitor circuit is disclosed. The variable capacitor circuit includes a plurality of MOS capacitors, each MOS capacitor being implemented by a MOS transistor with the gate terminal connected to a first voltage signal and with the drain terminal shorted with the source terminal and connected to a second voltage signal, said MOS capacitors being connected in parallel through the gate terminal connected to the first voltage signal, and being operated in a cut-off region in which the equivalent capacitance of each MOS capacitor remains substantially constant for variations of the first voltage signal.

10 Claims, 2 Drawing Sheets

(51) Int. Cl.
  *A61B 5/04* (2006.01)
  *A61B 5/0402* (2006.01)
  *A61B 5/053* (2006.01)
  *H01L 27/08* (2006.01)
  *H03F 1/56* (2006.01)
  *H03F 3/45* (2006.01)

(52) U.S. Cl.
  CPC ........ *A61B 5/0531* (2013.01); *H01L 27/0811* (2013.01); *H03F 1/56* (2013.01); *H03F 3/45475* (2013.01); *H03F 2200/213* (2013.01); *H03F 2200/261* (2013.01); *H03F 2203/45538* (2013.01); *H03F 2203/45544* (2013.01); *H03F 2203/45548* (2013.01); *H03F 2203/45576* (2013.01)

(58) Field of Classification Search
  USPC .......................................................... 257/312
  See application file for complete search history.

(56) References Cited

U.S. PATENT DOCUMENTS

| | | | |
|---|---|---|---|
| 5,238,001 A | 8/1993 | Gallant et al. | |
| 5,801,411 A | 9/1998 | Klughart | |
| 6,351,020 B1 | 2/2002 | Tarabbia | |
| 7,489,958 B2 | 2/2009 | Diab et al. | |
| 2001/0000414 A1 | 4/2001 | Fukayama | |
| 2001/0021813 A1 | 9/2001 | Yonce | |
| 2003/0171661 A1 | 9/2003 | Tong | |
| 2003/0189466 A1* | 10/2003 | Kitamura | 331/100 |
| 2004/0080363 A1* | 4/2004 | Yabe | H03F 1/305 327/546 |
| 2005/0258866 A1* | 11/2005 | Mandegaran | H03K 19/00315 326/82 |
| 2006/0097811 A1* | 5/2006 | Nakamura | H03B 5/1228 331/167 |
| 2006/0208816 A1* | 9/2006 | Ohshima et al. | 331/158 |
| 2007/0103248 A1* | 5/2007 | Nakamura | H03D 3/007 331/167 |
| 2007/0142735 A1 | 6/2007 | Shin et al. | |
| 2007/0189085 A1* | 8/2007 | Bang | G11C 5/147 365/189.09 |
| 2007/0268272 A1* | 11/2007 | Perski | G06F 3/044 345/173 |
| 2008/0079444 A1* | 4/2008 | Denison | G01D 5/24 324/679 |
| 2008/0081958 A1* | 4/2008 | Denison | A61N 1/3706 600/300 |
| 2008/0180278 A1* | 7/2008 | Denison | A61N 1/3702 340/870.18 |
| 2009/0066433 A1* | 3/2009 | Yamamoto | 331/182 |
| 2009/0082691 A1* | 3/2009 | Denison | A61B 5/04004 600/544 |
| 2009/0082829 A1* | 3/2009 | Panken | A61N 1/3606 607/45 |
| 2009/0168863 A1* | 7/2009 | Zolfaghari | H04B 1/0483 375/232 |
| 2009/0205436 A1* | 8/2009 | Garverick | G01L 19/086 73/777 |
| 2010/0141336 A1* | 6/2010 | Zhang | H03D 3/004 329/325 |
| 2010/0226166 A1 | 9/2010 | Jung | |
| 2010/0315102 A1 | 12/2010 | Portmann | |
| 2011/0160716 A1* | 6/2011 | Govari | A61B 18/1492 606/33 |
| 2011/0267212 A1* | 11/2011 | Denison | 341/122 |
| 2012/0068769 A1* | 3/2012 | Wang | H03F 1/342 330/260 |
| 2012/0166122 A1* | 6/2012 | Bottinelli | G01R 33/09 702/85 |
| 2013/0116577 A1 | 5/2013 | Yazicioglu et al. | |

OTHER PUBLICATIONS

European Search Report, European Patent Application No. 12191680.3 dated Mar. 7, 2013.
Kim, Sunyoung et al., "A 2.4uA Continuous-Time Electrode-Skin Impedance Measurement Circuit for Motion Artifact Monitoring in ECG Acquisition Systems", 2010 Symposium on VLSI Circuits/ Technical Digest of Technical Papers, Jun. 16, 2010, pp. 219-220.
European Search Report, European Patent Application No. 12007611.2, dated Aug. 27, 2015.

* cited by examiner

VARIABLE CAPACITOR CIRCUIT AND METHOD

CROSS-REFERENCE TO RELATED APPLICATIONS

This application claims priority under 35 U.S.C. §119(e) to U.S. Provisional Patent Application Ser. No. 61/557,060, filed on Nov. 8, 2011, and entitled "Biomedical Acquisition System for Evaluating and Detecting Biopotential Electrical Signals", the full disclosure of which is incorporated herein by reference.

BACKGROUND

1. Technical Field

The present disclosure is related to electrical circuits and more specifically to a variable capacitor circuit.

2. Technical Background

Variable capacitor arrays known in the art are described, for example, in U.S. Patent Application Pub. No. 2007/0268272 A1. However, the proposed solution involves, among other drawbacks, the use of on-off switches which are not suitable for capacitance mismatch compensation in certain biomedical signal acquisition circuits, such as circuits for the measurement and analysis of electrocardiogram (ECG) or electroencephalography (EEG) signals.

OVERVIEW

According to an example embodiment of the present disclosure, a variable capacitor circuit is provided. The variable capacitor circuit may comprise a plurality of MOS capacitors, each MOS capacitor being implemented by a MOS transistor with the gate terminal connected to a first voltage signal and with the drain terminal shorted with the source terminal and connected to a second voltage signal, said MOS capacitors being connected in parallel through the gate terminal connected to the first voltage signal, and being operated in a cut-off region in which the equivalent capacitance of each MOS capacitor remains substantially constant for variations of the first voltage signal.

According to an example embodiment, the value of the second voltage signal may be restricted to two voltage values lying within the cut-off region. According to another example embodiment, the values of the second voltage signal are 0V or 0.5V. Other values are possible as well. According to yet another example embodiment, the two values are chosen such that the equivalent capacitance of each MOS capacitor varies in the sub femtoFarad range. According to still another example embodiment, the total equivalent capacitance of the variable capacitor circuit is controlled by a digital signal.

According to another example embodiment, the MOS capacitors of the variable capacitor circuit are implemented with binary scaled sizes such that the equivalent capacitance of the MOS capacitors follows a binary arrangement.

According to still another example embodiment, the MOS transistor is a pMOs transistor and is operated for first voltage signals close to a ground rail satisfying the cut-off requirement. According to another example embodiment, the MOS transistor is an nMOs transistor and is operated for first voltage signals close to a positive supply rail.

According to another example embodiment, a biomedical signal acquisition circuit is provided. This biomedical acquisition circuit may comprise an instrumentation amplifier and a variable capacitor circuit according to an exemplary embodiment of the disclosure connected to each input line of the instrumentation amplifier. According to still another example embodiment, the variable capacitor circuit is connected to the input line of the instrumentation amplifier through the first voltage signal terminal.

According to another example embodiment, a method for compensating a capacitance mismatch between the input lines of an instrumentation amplifier is provided. The method may comprise: connecting a variable capacitor circuit according to an example embodiment of the disclosure to each input line of the instrumentation amplifier and changing the equivalent capacitance of the variable capacitor circuit so as to balance the parasitic loads on both input lines. According to yet another example embodiment, the step of changing the equivalent capacitance of the variable capacitor circuit is done by applying a digital signal to variable capacitor circuit.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

The disclosure will be further elucidated by means of the following description and the appended figures. Various exemplary embodiments are described herein with reference to the following figures, wherein like numerals denote like entities. The figures described are schematic and are non-limiting. Further, any reference signs in the claims shall not be construed as limiting the scope of the present disclosure. Still further, in the different figures, the same reference signs refer to the same or analogous elements.

DETAILED DESCRIPTION

Figure 1:
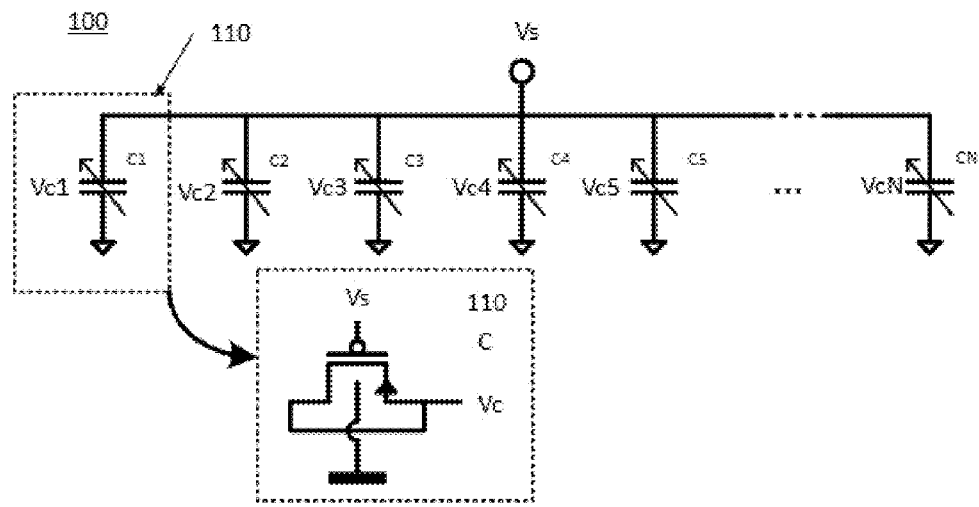
FIG. 1 shows a first example embodiment of a variable capacitor circuit according to an example of the present disclosure.
Figure 2:
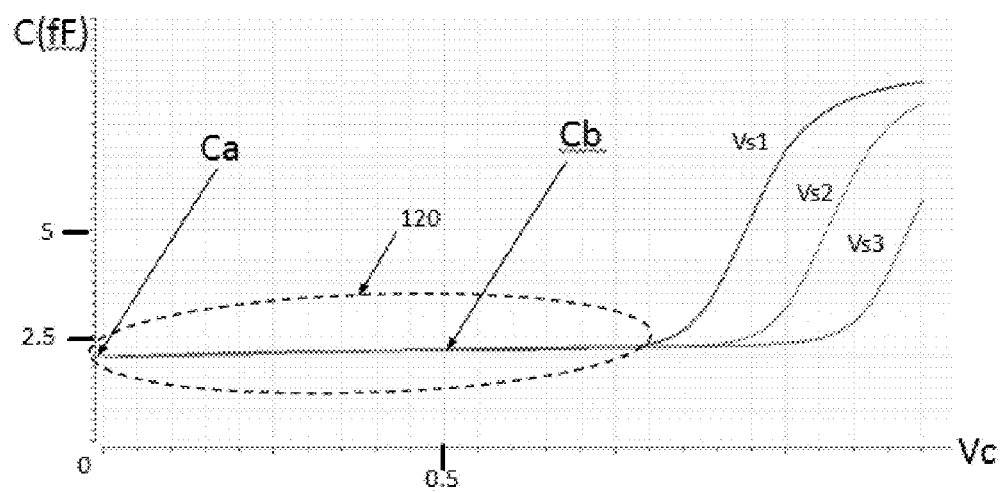
FIG. 2 shows an equivalent capacitance of an example MOS transistor as a function of several voltage signals.

FIG. 1 shows a first example embodiment of a variable capacitor circuit 100 according to an example of the present disclosure, comprising a plurality of variable MOS capacitors 110 connected in parallel. Each MOS capacitor 110 is driven by a control voltage Vc and a signal voltage Vs. The signal voltage Vs is connected to the gate, while the drain and source are shorted to the control voltage Vc. Each MOS capacitor 110 presents an equivalent capacitance C that depends on the values of the control voltage Vc and the signal voltage Vs, for example, as shown in FIG. 2.

According to an example embodiment of the disclosure, the MOS transistor is operated in the cut-off region 120, so that its equivalent capacitance C is small and remains substantially independent of the signal voltage Vs. According to an example embodiment of the disclosure, the equivalent capacitance C of a MOS capacitor 110, when operated in the cut-off region 120, remains substantially constant for large variations of the signal voltage Vs, for example even for a signal voltage Vs greater than 300 mVpp. According to another example embodiment of the disclosure the equivalent capacitance difference between two operating regions in the cut-off region 120 can be made to lie in the sub femtoFarad (fF) range (and, for example, as small as 0.1 fF).

According to another example embodiment of the disclosure, the control voltage Vc of each MOS capacitor 110 of the variable capacitor circuit 100 is restricted to just two voltage values within the cut-off region 120. According to one example embodiment, the control voltage Vc for each MOS transistor can be chosen to be either a first value of, for example 0V, or a second value of, for example 0.5V, so that the equivalent capacitance of each MOS capacitor 110 is either a first equivalent capacitance Ca, e.g. of 2.2 fF, when the control voltage Vc is 0V, or a second equivalent capacitance Cb, e.g. of 2.3 fF, when the control voltage Vc is 0.5V. It shall be then noted that, according to the example embodiment, the equivalent capacitance difference presented by the MOS capacitors 110 when operated with a first or a second control voltage value is of 0.1 fF. This advantageously allows for digital control and/or for a dynamical change or tuning of the equivalent capacitance presented by the variable capacitor circuit 100 according to an example of the disclosure. According to an example embodiment, the total equivalent capacitance of the variable capacitor circuit 100 can be controlled by a digital signal applied to the control voltage Vc input of the MOS transistors, so that their equivalent capacitance can be switched between two capacitance values.

According to another example embodiment of the disclosure, the MOS capacitors 110 of the variable capacitor circuit 100 are implemented with binary scaled sizes $C_{tot}$, so that the equivalent capacitance of the MOS capacitors follows a binary arrangement, for example, for $C_i$ where i is an index from 1 to positive integer n, $C1=C_0$, $C2=2C_0$, $C3=4C_0$, $C4=8C_0$, $C5=16C_0$, and so on.

According to another example embodiment of the disclosure, the total equivalent capacitance value $C_{tot}$ of the variable capacitor circuit 100 is given by:

$$C_{tot} = \sum_{i=1}^{n} C_{i,0} + V_{ci}\Delta C_i \text{ where } V_{ci} \in [0, 1] \text{ and } \Delta C_i = 2\Delta C_{i-1}$$

If the digital control signal $V_c$ is low, the capacitance value is $C_{i,0}$, if $V_c$ is high, the capacitance value will be $C_{i,0}+\Delta C_i$. According to another example embodiment, the difference between these two values $\Delta C_i$ can be made very small thus advantageously yielding a tunable variable capacitor circuit 100 with subfemtoFarad accuracy.

According to an example embodiment of the disclosure, the MOS capacitors 110 are implemented as pMOS transistors, in which the corresponding behavior according an example embodiment of the disclosure shown with reference to FIG. 2 is achieved when operated for input signal levels close to the ground rail satisfying the cut-off requirement. According to another example embodiment of the disclosure, the MOS capacitors 110 may be implemented as nMOS transistors, when operated for input signal levels closer to the positive supply rail.

According to an example embodiment of the disclosure, a variable capacitor circuit 100 may function as an ultra-precise tunable capacitor achieving a capacitance resolution in the range of sub femtoFarads. According to another example embodiment, said tunable capacitance may be digitally controlled. According to another example embodiment, the variable capacitor circuit 100 advantageously behaves as a linear capacitor without significant capacitance changes for large variations of the input voltage signal Vs. According to another example embodiment, the variable capacitor circuit 100 may be implemented with minimal routing and area overhead. According to another example embodiment, the variable capacitor circuit 100 allows for compensation of capacitance mismatch by capacitance tuning after the electrical circuit manufacturing process.

Figure 3:
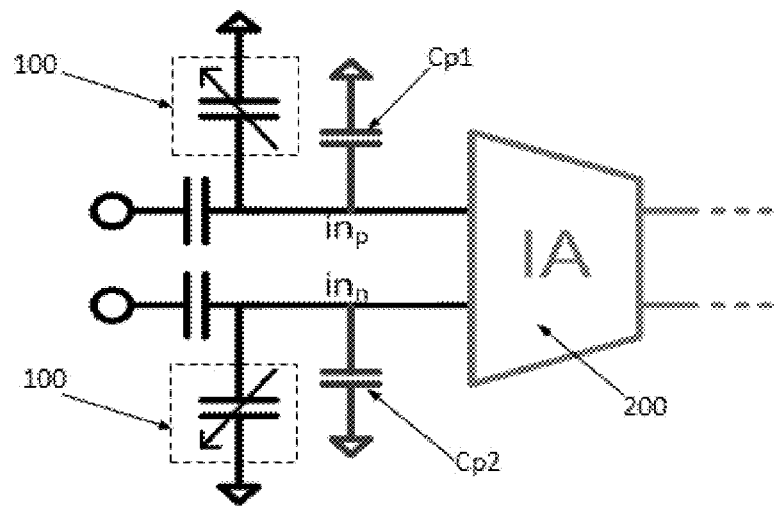
FIG. 3 shows an instrumentation amplifier with a variable capacitor circuit according to an example of the present disclosure to maximize the CMRR.

FIG. 3 shows an exemplary application according to an example embodiment of the disclosure, in which an instrumentation amplifier 200 uses two variable capacitor circuits 100 to reduce the capacitance mismatch between the input lines inp, inn to that instrumentation amplifier 200. Capacitance mismatch between input lines to instrumentation amplifiers due to parasitic capacitances Cp1, Cp2 is a typical problem in biomedical signal acquisition circuits, and can be solved, according to an example embodiment of the disclosure, by adding a variable capacitor circuit 100 to each instrumentation amplifier input line, in order to balance the parasitic loads on both input lines. Advantageously, the variable capacitor circuit 100 is connected to the input line of the instrumentation amplifier through voltage signal Vs terminal, so that the signals flowing through the input line do not affect the equivalent capacitance of variable capacitor circuit 100. Also advantageously, the variable capacitor circuit 100 does not introduce any non-linear characteristics to the signal path when the equivalent capacitance is changed or tuned.

According to an example embodiment of the disclosure, after manufacturing process of a biomedical signal acquisition circuit comprising an instrumentation amplifier 200 and a variable capacitor circuit 100 connected to each input line of the instrumentation amplifier, the variable capacitor circuits 100 is tuned in capacitance value to compensate parasitic mismatch and maximize the common-mode rejection ratio (CMRR).

Figure 4:
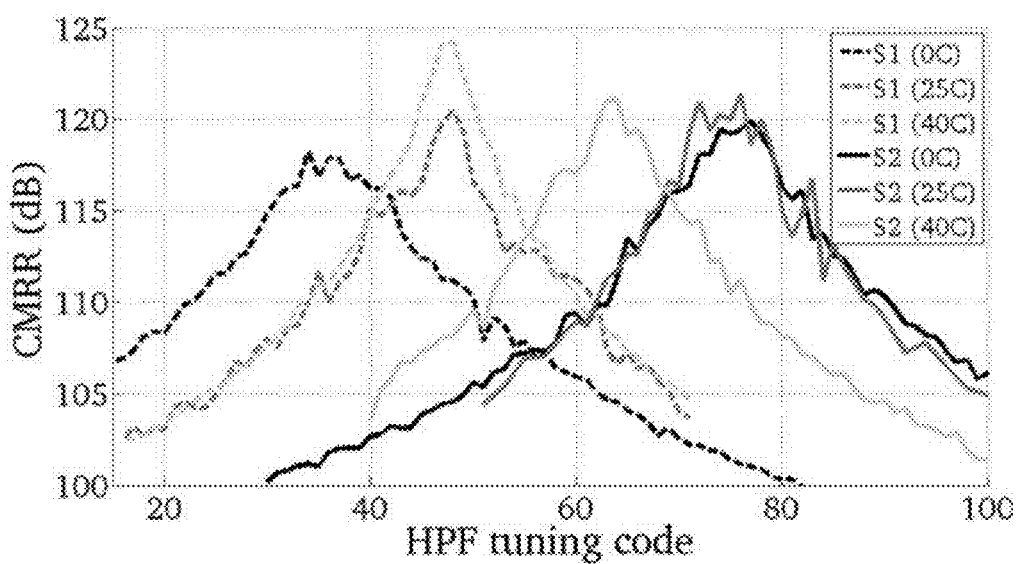
FIG. 4 illustrates the measured CMRR for two samples as a function of the digital control code of the variable capacitor circuit according to an example of the present disclosure.

FIG. 4 shows how the CMRR can be tuned after manufacturing. It illustrates the measured CMRR for two samples as a function of the digital control code of the variable capacitor circuits 100. Within the 0-40° C. temperature range, the optimum value shifts slightly but still 115 dB can be guaranteed. Alternatively a periodic recalibration based on a temperature measurement and a LUT could be implemented.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

The invention claimed is:

1. A method for compensating a capacitance mismatch between input lines of an instrumentation amplifier, the method comprising:

operating a plurality of MOS capacitors of a variable capacitor circuit in a cut-off region in which an equivalent capacitance of each MOS capacitor remains substantially constant for variations of a first voltage signal, wherein each MOS capacitor is implemented by a MOS transistor with a gate terminal connected to the first voltage signal and a drain terminal shorted with a source terminal and connected to a second voltage signal, wherein the MOS capacitors are connected in parallel through the gate terminal connected to the first voltage signal, and wherein operating the plurality of MOS capacitors includes restricting the second voltage signal to two voltage values lying within the cut-off region; and changing the equivalent capacitance of the variable capacitor circuit so as to balance parasitic loads on both input lines, wherein changing the equivalent capacitance comprises controlling the second voltage signal between the two voltage values such that the equivalent capacitance is controllably adjustable within a sub-femtoFarad range.

2. The method of claim 1, wherein changing the equivalent capacitance of the variable capacitor circuit further comprises applying a digital control code, $V_c$, to the variable capacitor circuit.

3. The method of claim 1, further comprising receiving, via at least one input line of the instrumentation amplifier, at least one signal selected from the group consisting of an electrocardiogram (ECG) signal and an electroencephalography (EEG) signal.

4. The method of claim 2, wherein the MOS capacitors of the variable capacitor circuit are implemented with binary scaled sizes such that the equivalent capacitance of the MOS capacitors follows a binary arrangement, and wherein the total equivalent capacitance comprises:

$$C_{tot} = \sum_{i=1}^{n} C_{i,0} + V_{ci}\Delta C_i$$

where $V_{ci} \in [0, 1]$ $\Delta C_i = 2\Delta C_{i-1}$.

5. The method of claim 2, further comprising receiving data indicative of a temperature of the variable capacitor and adjusting the digital control code based on at least the received data and a look-up table.

6. The method of claim 1, wherein a variable capacitor circuit is connected to each input line of the instrumentation amplifier, wherein changing the equivalent capacitance of the respective variable capacitor circuits comprises maximizing the common-mode rejection ratio (CMRR) of the instrumentation amplifier.

7. The method of claim 1, wherein the variable capacitor is connected to the input line of the instrumentation amplifier through the gate terminal.

8. The method of claim 1, wherein said values of the second voltage signal are selected from the group of 0V and 0.5V.

9. The method of claim 1, wherein the MOS transistor is a pMOS transistor and is operated for first voltage signals close to a ground rail satisfying a cut-off requirement.

10. The method of claim 1, wherein the MOS transistor is an nMOS transistor and is operated for first voltage signals close to a positive supply rail.

* * * * *